United States Patent [19]

Gilbert et al.

[11] Patent Number: 5,330,893

[45] Date of Patent: Jul. 19, 1994

[54] USE OF SUPEROXIDE DISMUTASE IN SPECIMEN DILUENT

[75] Inventors: Adrienne L. Gilbert, Buffalo Grove; James L. Stewart, Gurnee; Sarah L. Kidd, Chicago; George J. Dawson, Libertyville, all of Ill.

[73] Assignee: Abbott Laboratories, Abbott Park, Ill.

[21] Appl. No.: 59,868

[22] Filed: May 10, 1993

Related U.S. Application Data

[63] Continuation of Ser. No. 647,374, Jan. 25, 1991, abandoned.

[51] Int. Cl.$^5$ .................... C12Q 1/26; C12N 9/02
[52] U.S. Cl. .................... 435/7.1; 435/189; 435/7.92; 435/7.94; 435/7.95
[58] Field of Search .......... 435/7.1, 189, 172.3, 435/7.92, 7.94, 7.95; 436/538

[56] References Cited

FOREIGN PATENT DOCUMENTS 0318216 5/1989 European Pat. Off. ..... C12N 15/00

OTHER PUBLICATIONS

Y. Ikeda, et al., "Antibody to Superoxide Dismutase, Autoimmune Hepatitis, and Antibody Tests for Hepatitis C Virus", Lancet 335:1345–1346 (Jun., 1990).

I. G. McFarlane, et al., "Hepatitis C Virus Antibodies in Chronic Active Hepatitis: Pathogenic Factor or False-Positive Result?", Lancet 335:754–57 (Mar., 1990).

Young et al. (1983), Science 222: 778–782.

Hallewell et al. (1985), Nucl. Acids Res. 13(6): 2017–2034.

*Primary Examiner*—Richard A. Schwartz
*Assistant Examiner*—Philip W. Carter
*Attorney, Agent, or Firm*—Priscilla E. Porembski; Joan Eggert

[57] ABSTRACT

An improved method for detecting antibodies is disclosed. The method involves the steps of a) mixing the specimen with a diluent comprising superoxide dismutase, and b) contacting the diluted specimen with at least one recombinant antigen expressed as a fusion protein with superoxide dismutase.

9 Claims, 1 Drawing Sheet

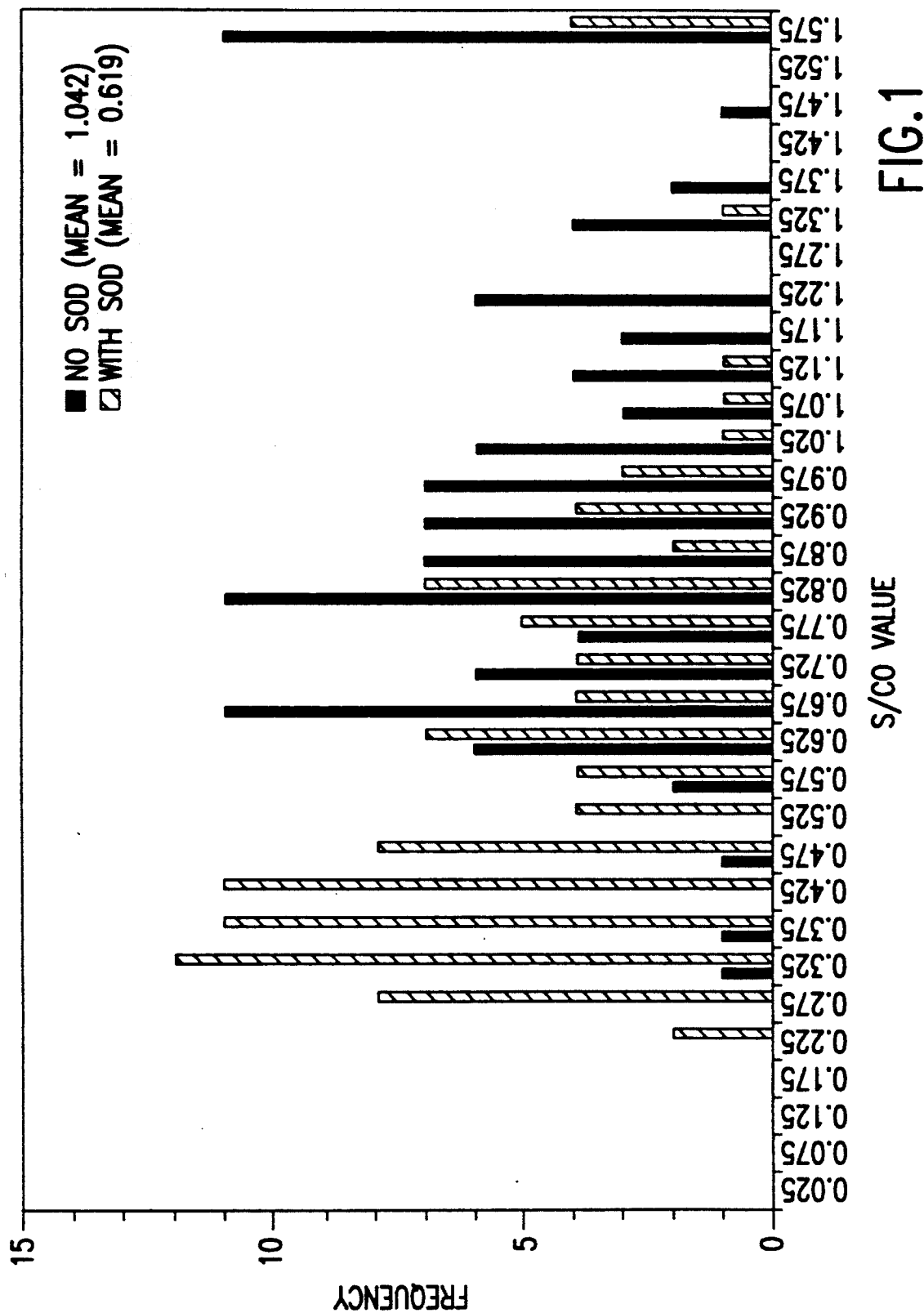

USE OF SUPEROXIDE DISMUTASE IN SPECIMEN DILUENT

This application is a continuation of application Ser. No. 07/647,374, filed Jan. 25, 1991, now abandoned.

BACKGROUND OF THE INVENTION

1. Field of the Invention

The present invention relates generally to a method for improving the specificity of immunoassays, and more particularly, relates to a method for adding superoxide dismutase to a specimen diluent to increase the specificity of immunoassays which utilize recombinant antigens expressed as a fusion protein with superoxide dismutase.

2. Description of Related Art

Historically, immunoassays have been known to be prone to false positive reactions. Viral lysates or recombinant protein preparations, which comprise the antigen solutions which are utilized on the solid support, can also contain other proteins. These other proteins can bind to the solid support, introducing the possibility of reactivity with antibodies in the patient's sample. Alternatively, a component in the patient's sample can bind to the solid support and interfere with the assay.

For example, McFarlane et al., *Lancet* (1990) 335:754–57, reported a high prevalence of antibody to hepatitis C virus (HCV) in patients with autoimmune chronic active hepatitis (AI-CAH). They suggested that the serum of AI-CAH patients may contain a component that gives false-positive results in the assay. McFarlane et al. surmised that the assay might have been non-specifically detecting IgG since they saw a correlation between IgG levels and OD values, or that factors contained in the patient sera were responsible for the results, such as an antibody against some other pathogen which cross-reacts with the antigen used in the assay, or a component which adheres to the solid phase and binds IgG.

In addition, some false positive results are due to cross-reactivity between the patient sera and the fusion protein used to express the recombinant antigen utilized in the assay. For example, components in patient sera can react with *E. coli* proteins used in recombinant HIV assays. This reactivity can be expected because *E. coli* organisms, which constitute the majority of the intestinal flora of man, are foreign to the human body, and the human immune system mounts an immunogenic response against the existant antigen.

On the other hand, it normally is unexpected that humans would possess antibodies against superoxide dismutase (SOD). Superoxide dismutases are enzymes which exist in some form in almost every living organism. In humans, superoxide dismutase catalyzes the conversion of superoxide ($O_2-$) to oxygen and $H_2O_2$ (Fridovich, *Adv. Enzymol.* (1974) 41:35). Phagocytes use superoxide and other microbicidal oxidants to destroy ingested microorganisms. These oxidants are produced during phagocytosis and are characterized by unusually high reactivity and the presence of an unpaired electron. If left unchecked, the oxidants may damage host cells and tissues; however, phagocytes possess several means of defending themselves against the endogenously produced oxidants. One of these means is the enzyme superoxide dismutase, which scavenges superoxide before it can harm host cells and tissues.

There is a substantial need, therefore, for an improved method for detecting antibodies by increasing assay specificity.

SUMMARY OF THE INVENTION

The present invention provides a method for detecting antibodies in a specimen which comprises the steps of a) mixing the specimen with a diluent comprising superoxide dismutase, and b) contacting the diluted specimen with at least one recombinant antigen expressed as a fusion protein with superoxide dismutase.

BRIEF DESCRIPTION OF THE DRAWINGS

FIG. 1 illustrates the effect of SOD addition on a population of HCV false positive specimens.

DETAILED DESCRIPTION OF THE INVENTION

The present invention provides an improvement to methods for detecting antibodies in a specimen from an individual, wherein a recombinant antigen employed in the method is expressed as a fusion protein by a vector and wherein the recombinant antigen is encoded with the superoxide dismutase gene. The improvement comprises the step of mixing the specimen with a diluent containing superoxide dismutase.

It has been discovered that it is especially advantageous to add SOD to a diluent (hereinafter defined) to improve the detection of antibodies by increasing assay specificity. This is because it has unexpectedly been discovered that humans have antibody to SOD. Immunoassays can employ recombinant antigens which are expressed as a fusion protein by a vector in which the antigen is encoded with the superoxide dismutase gene. (See EP 196056, published Oct. 1, 1986.) Therefore, those assays which utilize SOD fusion proteins can exhibit an interfering reaction with anti-SOD antibodies in patient samples. SOD can be added to the diluent in concentrations ranging from about 0.001 g/L to about 1 g/L, more preferably from about 0.005 g/L to about 0.5 g/L, and most preferably from about 0.01 g/L to about 0.1 g/L. The SOD can be added as a purified or partially purified protein from a yeast extract.

For example, currently licensed HCV enzyme-linked immunosorbent assays (ELISA) utilize a yeast derived antigen (c100-3) expressed as a fusion protein with recombinant human superoxide dismutase (SOD). The antigen is designated SOD-c100-3. (See EP 318216, published May 31, 1989.) We have discovered unexpectedly that normal, random blood donors exhibit anti-SOD activity. These donor populations are characterized by individuals considered at low risk of HCV exposure or infection. For example, in a clinical trial of 13,153 random blood donors using a HCV enzyme immunoassay (EIA) commercially available from Abbott Laboratories, Abbott Park, Ill, Abbott HCV EIA, 100 samples were detected as repeatedly reactive in the assay. Only 38 of the 100 samples could be confirmed positive for anti-HCV using alternative testing methods. These data suggested a false positive rate as high as 62%.

A false positive result is defined herein as one in which a sample is repeatably reactive in an ELISA or EIA but is not confirmed by alternative methods for the presence of HCV antibodies. Alternative testing methods include synthetic peptide EIAs, antibody blocking procedures and recombinant immunoblot assays.

In accordance with the present invention, a "diluent" is defined herein as an aqueous solution of buffer(s) and salt(s) as well understood in the art and illustrated infra. While a preferred buffer is Tris[hydroxymethyl]aminomethane, commercially available under the trade designation Tris from Sigma Chemical Co., St. Louis, Mo., suitable buffers include, but are not limited to, buffers such as phosphate, HEPES (N-[2-hydroxyethyl]piperazine-N'-[2-ethanesulfonic acid]), PIPES (piperazine-N,N'-bis[2-ethanesulfonic acid]), CAPS (3-[cyclohexylamino]-1-propanesulfonic acid) and MOPES (3-[N-morpholino]propanesulfonic acid). Suitable salts include sodium chloride (NaCl) and salts such as phosphate salts and sulfate salts.

In addition, various animal sera, detergents, blocking agents and other components can be added to improve specificity. For example, animal serum proteins such as bovine serum, bovine serum albumin (BSA), fetal calf serum and goat serum can be added in concentrations ranging from about 0.5% v/v to about 50% v/v. Biological detergents such as polyoxyethylenesorbitan, commercially available as Tween® 20, polyoxyethylene ether, commercially available as Triton® X-100, Nonidet P-40 (an octylphenol-ethylene oxide condensate), sodium dodecyl sulfate (SDS) or N-lauroylsarcosine (N-dodecanoyl-N-methylglycine) can be added in concentrations ranging from about 0.01% v/v to about 5% v/v. Chelators such as ethylenediaminetetraacetic acid (EDTA) and ethylene glycol-bis($\beta$-aminoethylether) N,N,N',N'-tetraacetic acid (EGTA) can be added in concentrations ranging from about 2 mM to about 20 mM.

In order to neutralize nonspecific reactions due to other proteins contained in the viral lysates or recombinant proteins that comprise the antigen solutions employed on the solid support, a lymphocyte lysate solution, for example, human T-lymphocyte solution or a host cell lysate solution such as an E. coli lysate solution, can be added in concentrations typically ranging from about 0.01% v/v to about 10% v/v. Preservatives such as sodium azide can also be added.

METHODS

Recombinant SOD

A synthetic sequence of the DNA was prepared using a published DNA sequence (see PNAS 80:5465–69, *Nuc. Acid Res.* 12:9349–63). The sequence was modified to facilitate cloning using the FokI bridge mutagenesis protocol published by Bolling et al. (*Gene* (1988) 68:101–07). The final sequence of the synthetic gene yielded the identical amino acid sequence to the native gene. The synthetic gene was fused with the regulatory genes of the sorbitol dehydrogenase gene from yeast and inserted into a yeast plasmid. The resultant plasmid containing the gene for SOD, SOD 8-3, was transformed into a mutant yeast strain capable of growing on sorbitol as a carbon source.

The mutant yeast cells containing plasmid SOD 8-3 were grown, harvested and concentrated into a cell paste to be purified. The yeast cell paste was homogenized to break open the cells. The homogenate then was clarified. The clarified homogenate was heated to approximately 85°–95° C. for about five minutes and clarified again. The homogenate was passed over an anion exchange column. The column was extensively washed, and the SOD was eluted by step elution with salt. The eluate was concentrated to from about 1 mg/mL to about 20 mg/mL and then was sterilely filtered.

Specimen Diluent

The sample diluent comprising 10% (v/v) bovine serum and 20% (v/v) goat serum in 20 mM Tris phosphate buffer containing 0.2% (v/v) Triton X-100, 1% (w/v) BSA, 1% *E. coli* lysate, 100 ug/mL CKS lysate and 150 ug/mL yeast extract was prepared. This diluent then was tested as described hereinbelow.

The present invention will now be described by way of Examples which are meant to illustrate, but not to limit, the spirit and scope of the invention.

EXAMPLE 1

Random Volunteer Donors

In order to assess false reactions due to SOD cross-reactivity, follow-up testing was conducted on seventeen repeatably reactive samples out of 2000 random volunteer serum donors tested at a clinical site, using the Abbott HCV EIA which utilizes the SOD-c100-3 antigen.

Eight of the 17 samples were confirmed to be positive for antibodies to HCV by the alternative testing methods described above. Seven of the remaining 9 samples believed to be false positive were subsequently retested in the assay, in the presence and absence of the previously described recombinant human SOD. Two samples were not retested due to insufficient volume of sample.

Briefly, the recombinant SOD described above was added to the specimen diluent of the Abbott HCV EIA at a concentration of 30 ug/mL. The assay procedure was followed according to the manufacturer's instructions. The presence of cross-reacting antibodies to SOD was indicated by a significant reduction in abosorbance upon addition of the soluble SOD. Samples were considered SOD reactive if they were neutralized (i.e., tested negative) in the presence of SOD.

As summarized in Table 1, 6 of the 7 samples (86%) were neutralized by adding SOD; the remaining sample showed a reduction in absorbance but remained above the assay cutoff. This data suggested that the majority of false positive specimens identified (i.e., at least 6 of 9) were attributable to cross-reactivity to the SOD portion of the fusion protein. This data also demonstrated that soluble SOD was effective in blocking reactivity to SOD in the EIA method.

TABLE 1

| Clinical Site | No. Repeat Reactive | No. Confirmed | No. False Positive | No. SOD Reactive* |
|---|---|---|---|---|
| 1 | 17 | 8 | 9 | 6 |
| 2 | 17 | 7 | 10 | 6 |

*7 of 9 false positive samples were tested at site 1; 8 of 10 were tested at site 2.

Similar data was obtained from a second clinical site. As summarized in Table 1, 6 of 8 false reactive samples (75%) were neutralized by adding SOD.

EXAMPLE 2

Further Testing

Further testing was conducted on 3 SOD reactive specimens to demonstrate the specificity of the soluble SOD for neutralizing the cross-reactive antibodies. These samples were tested in parallel using specimen diluents containing: 1) no yeast extract 2) 200 or 400 $\mu$g/ml of yeast extract which did not contain recombinant SOD and 3) 200 or 400 ug/ml of yeast extract which contained recombinant SOD.

The presence of anti-HCV antibodies was determined by relating the absorbance at 492 nm of the specimen to a cutoff value. The cutoff value was the absorbance of the negative control mean plus 0.25 times the absorbance of the positive control mean. Then, a ratio of the absorbance value of the specimen to the cutoff value (S/CO) was determined. Specimens with S/CO ratios greater than or equal to 1 were considered reactive. Those specimens with S/CO ratios less than 1 were considered nonreactive.

TABLE 2

| Sample | No Yeast | Yeast without SOD 200 | 400 | Yeast with SOD 200 | 400 |
|---|---|---|---|---|---|
| 1 | 1.30 | 1.15 | 1.04 | 0.65 | 0.63 |
| 2 | 0.90 | 1.04 | 0.96 | 0.54 | 0.51 |
| 3 | 1.57 | 1.66 | 1.46 | 0.69 | 0.67 |

Concentrations of yeast extract in ug/ml; all values reported as S/CO ratio.

As shown in Table 2, the samples were reactive or borderline nonreactive when tested with diluents containing no yeast or the control yeast which did not contain SOD. All three specimens were negative when tested with the diluent containing yeast extract with soluble SOD. This indicated that the SOD was directly responsible for blocking the false positive reaction in the Abbott HCV EIA. This data also suggested that soluble SOD is useful as a means to block false positive reactions in immunoassays which use SOD fusion proteins.

EXAMPLE 3

Abbott HCV Second Generation EIA

The Abbott HCV second generation EIA (Second Gen) uses multiple recombinant antigens representing both structural and non-structural regions of the HCV genome. One of the antigens used in the assay is the SOD-c100-3 described hereinabove. This assay also includes soluble SOD as a component in the specimen diluent, at a concentration of 30 ug/mL.

In order to test the efficacy of the soluble SOD in improving assay specificity, 185 serum specimens which previously showed false positive reaction in the Abbott HCV EIA were tested by Second Gen. These samples were sourced from random volunteer blood donors in Australia. The samples also were tested by the Second Gen method without SOD in the speciment diluent as a control. Briefly, 10 uL of specimen was diluted with 400 uL of the specimen diluent described hereinabove. Two hundred microliters of diluted specimen were incubated with a polystyrene bead for about 1 hour at approximately 40° C. A mixture of structural and non-structural HCV antigens, including SOD-c100-3, was bound to the bead. The bead was washed, and 200 uL of a goat anti-human IgG, horseradish peroxidase labeled conjugate were added to and incubated with the bead for about 30 minutes at approximately 40° C. The bead was washed, and color was developed by incubating the bead with o-phenylenediamine (OPD) substrate solution. After about 30 minutes, the reaction was stopped with 1N sulfuric acid. The absorbance at 492 nm of the bead was measured.

TABLE 3

| | | With SOD Pos | Neg |
|---|---|---|---|
| Without SOD | Pos | 11 | 41 |
| | Neg | 5 | 128 |

As shown in Table 3, only 57 of the 185 HCV ELA positive samples were positive in the Second Gen assay, regardless of the presence of SOD. It was thought that this improvement in specificity was likely due to other improvements in the Second Gen assay format. Of the remaining 57 samples, 41 (72%) false positive reactions were eliminated with the addition of SOD to the specimen diluent. Thirty-two of the 41 samples showed substantial (>50%) reduction in absorbance in the presence of SOD. All five samples which were positive only with SOD in the diluent were borderline reactive and showed no significant change in reactivity as a function of SOD addition.

As seen in FIG. 1, SOD addition improved the specificity of the assay. FIG. 1 shows the frequency distribution of the Australian false positive samples by S/CO values in the presence and absence of SOD. Without SOD, the population is significantly elevated, having a mean S/CO value of 1.042. By adding SOD, the mean S/CO value substantially decreases to 0.619. Consequently, there is a significant downshift in the population and a substantial reduction in the number of false positives when SOD is added to the diluent.

What is claimed is:

1. In a method for detecting antibodies in a specimen which comprises contacting a diluted specimen with at least one recombinant antigen expressed as a fusion protein with superoxide dismutase, the improvement comprising mixing said specimen with a diluent comprising superoxide dismutase.

2. The method of claim 1, wherein said superoxide dismutase is a recombinant protein.

3. The method of claim 1, wherein the concentration of said superoxide dismutase is from about 0.001 g/L diluent to about 1.0 g/L diluent.

4. The method of claim 3, wherein the concentration of said superoxide dismutase is from about 0.01 g/L diluent to about 0.1 g/L diluent.

5. The method of claim 1, wherein said recombinant antigen is SOD-c100-3.

6. In a method for detecting anti-HCV antibodies in a specimen which comprises contacting a diluted specimen with at least one recombinant antigen expressed as a fusion protein with superoxide dismutase, the improvement comprising mixing said specimen with a diluent comprising superoxide dismutase.

7. The method of claim 6, wherein said recombinant antigen is SOD-c100-3.

8. The method of claim 1, wherein said superoxide dismutase is at a concentration of about 30 µg/ml.

9. The method of claim 6, wherein said superoxide dismutase is at a concentration of about 30 82 g/ml.

* * * * *

UNITED STATES PATENT AND TRADEMARK OFFICE
CERTIFICATE OF CORRECTION

PATENT NO. : 5,330,893

DATED : July 19, 1994

INVENTOR(S) : Adrienne L. Gilbert, James L. Stewart, Sarah L. Kidd, George J. Dawson It is certified that error appears in the above-identified patent and that said Letters Patent is hereby corrected as shown below:

Col. 6, line 61 change "82 g/ml" to -- µg/ml--.

Signed and Sealed this

Second Day of May, 1995

Attest:

BRUCE LEHMAN

Attesting Officer

Commissioner of Patents and Trademarks